(12) United States Patent
Biggs et al.

(10) Patent No.: US 8,702,670 B2
(45) Date of Patent: Apr. 22, 2014

(54) INTRAVAGINAL DEVICE WITH CONTROLLED EXPANSION

(75) Inventors: Jehann Biggs, Evanston, IL (US);
Samuel Carasso, Milltown, NJ (US);
Erin Marsee, Nicholasville, KY (US);
Tara Glasgow, New Hope, PA (US);
Julia Iris, North Wales, PA (US); Gina J. Marcus, Trenton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 970 days.

(21) Appl. No.: 11/172,310

(22) Filed: Jun. 30, 2005

(65) Prior Publication Data
US 2007/0005039 A1 Jan. 4, 2007

Related U.S. Application Data

(60) Provisional application No. 60/584,772, filed on Jun. 30, 2004.

(51) Int. Cl.
*A61F 13/20* (2006.01)

(52) U.S. Cl.
CPC ............. *A61F 13/20* (2013.01); *A61F 13/2071* (2013.01)
USPC ..................................... 604/385.17; 604/380

(58) Field of Classification Search
CPC ............................ A61F 13/20; A61F 13/2071
USPC ............... 604/385.17, 385.18, 904, 380, 382, 604/385.12
See application file for complete search history.

(56) References Cited

U.S. PATENT DOCUMENTS

| | | | | |
|---|---|---|---|---|
| 271,625 A | * | 2/1883 | Goff | 604/378 |
| 1,396,142 A | * | 11/1921 | Peerson | 19/93 |
| 1,555,708 A | * | 9/1925 | Gale | 604/373 |
| 1,726,339 A | * | 8/1929 | Burill | 604/374 |
| 1,926,900 A | | 9/1933 | Haas | |
| 1,932,383 A | * | 10/1933 | Richardson | 604/375 |
| 1,941,717 A | * | 1/1934 | Rabell | 604/377 |
| 1,977,133 A | * | 10/1934 | Linard | 604/363 |
| 1,978,806 A | * | 10/1934 | Medoff | 206/770 |
| 1,989,931 A | * | 2/1935 | Johnson | 206/326 |
| 2,057,206 A | * | 10/1936 | Pohl | 604/377 |
| 2,099,931 A | * | 11/1937 | Fourness | 604/364 |
| 2,123,750 A | * | 7/1938 | Schulz | 604/365 |
| 2,298,424 A | * | 10/1942 | Schreiber | 604/368 |

(Continued)

FOREIGN PATENT DOCUMENTS

EP 292831 A1 11/1988
JP 2004097304 A 4/2002

OTHER PUBLICATIONS

Search Report re: PCT/US2005/023812 dated Dec. 5, 2005.

*Primary Examiner* — Melanie Hand
*Assistant Examiner* — Paula Craig

(57) ABSTRACT

Controlled expansion of an intravaginal device can be achieved by selectively attaching either a primary or secondary cover to the primary absorbent device having a fluid storage element. We can determine that certain portions of the tampon will expand while other portions will be restricted to substantially the compressed structure. The primary cover can be attached to the primary absorbent device either before or after the absorbent device is compressed into final tampon form. The compression may be in the axial or radial direction or a combination of both directions. The secondary cover, if used, can be attached after the tampon pledget has been compressed into the final tampon form.

10 Claims, 3 Drawing Sheets

(56) References Cited

U.S. PATENT DOCUMENTS

| | | | | |
|---|---|---|---|---|
| 2,328,795 | A * | 9/1943 | Finks | 604/377 |
| 2,340,311 | A * | 2/1944 | Donovan | 604/363 |
| 2,464,310 | A * | 3/1949 | Harwood | 28/118 |
| 2,491,017 | A * | 12/1949 | Robinson | 604/364 |
| 2,734,505 | A * | 2/1956 | Parish | 604/363 |
| 2,782,458 | A * | 2/1957 | Emmert et al. | 264/137 |
| 2,808,832 | A * | 10/1957 | Myers et al. | 604/364 |
| 2,844,150 | A * | 7/1958 | Draghi | 600/572 |
| 2,845,070 | A * | 7/1958 | Lewing | 604/368 |
| 2,902,037 | A * | 9/1959 | Harwood et al. | 604/365 |
| 3,101,714 | A | 8/1963 | Stanley | |
| 3,422,496 | A | 1/1969 | Wolff et al. | |
| 3,595,236 | A * | 7/1971 | Corrigan et al. | 604/363 |
| 3,607,520 | A * | 9/1971 | Jones | 156/198 |
| 3,610,243 | A * | 10/1971 | Jones, Sr. | 604/375 |
| 3,624,746 | A * | 11/1971 | Grad et al. | 604/383 |
| 3,731,687 | A * | 5/1973 | Glassman | 604/379 |
| 3,738,364 | A * | 6/1973 | Brien et al. | 604/375 |
| 3,811,445 | A | 5/1974 | Dostal | |
| 3,812,856 | A * | 5/1974 | Duncan et al. | 604/364 |
| 3,815,601 | A * | 6/1974 | Schaefer | 604/15 |
| 3,850,160 | A * | 11/1974 | Denson | 600/572 |
| 3,854,481 | A * | 12/1974 | Messing | 604/380 |
| 3,946,737 | A * | 3/1976 | Kobler | 604/385.18 |
| 3,954,104 | A * | 5/1976 | Kraskin et al. | 604/15 |
| 3,971,378 | A | 7/1976 | Krantz | |
| 3,983,875 | A | 10/1976 | Truman | |
| 3,995,636 | A * | 12/1976 | Murray et al. | 604/286 |
| 4,077,409 | A * | 3/1978 | Murray et al. | 604/15 |
| 4,212,301 | A | 7/1980 | Johnson | |
| 4,266,546 | A * | 5/1981 | Roland et al. | 604/365 |
| 4,278,088 | A * | 7/1981 | Reeves et al. | 604/368 |
| 4,381,326 | A | 4/1983 | Kelly | |
| 4,743,237 | A * | 5/1988 | Sweere | 604/358 |
| 4,816,100 | A * | 3/1989 | Friese | 156/191 |
| 5,006,116 | A * | 4/1991 | Alikhan et al. | 604/365 |
| 5,165,152 | A | 11/1992 | Kramer et al. | |
| 5,374,258 | A * | 12/1994 | Lloyd et al. | 604/358 |
| 5,476,455 | A * | 12/1995 | Silber | 604/330 |
| 5,542,914 | A * | 8/1996 | Van Iten | 604/11 |
| 5,567,376 | A | 10/1996 | Turi et al. | |
| 5,609,586 | A * | 3/1997 | Zadini et al. | 604/358 |
| 5,755,706 | A * | 5/1998 | Kronenthal et al. | 604/358 |
| 5,911,712 | A | 6/1999 | Leutwyler et al. | |
| 6,039,716 | A | 3/2000 | Jessup et al. | |
| 6,177,608 | B1 * | 1/2001 | Weinstrauch | 604/380 |
| 6,183,436 | B1 * | 2/2001 | Korteweg et al. | 604/96.01 |
| 6,191,341 | B1 * | 2/2001 | Shippert | 604/383 |
| 6,206,867 | B1 | 3/2001 | Osborn, III et al. | |
| 6,258,075 | B1 * | 7/2001 | Taylor et al. | 604/385.18 |
| 6,310,269 | B1 | 10/2001 | Friese et al. | |
| 6,310,296 | B1 | 10/2001 | Nishi et al. | |
| 6,358,235 | B1 | 3/2002 | Osborn, III et al. | |
| 6,465,713 | B1 * | 10/2002 | Gell et al. | 604/383 |
| 6,554,814 | B1 | 4/2003 | Agyapong et al. | |
| 6,570,055 | B2 | 5/2003 | Yang et al. | |
| 6,860,874 | B2 * | 3/2005 | Gubernick et al. | 604/385.18 |
| 7,722,588 | B1 | 5/2010 | Johnson et al. | |
| 2001/0011169 | A1 | 8/2001 | Taylor et al. | |
| 2001/0014348 | A1 * | 8/2001 | Schoelling | 424/431 |
| 2002/0120246 | A1 * | 8/2002 | Buzot | 604/385.17 |
| 2002/0123731 | A1 | 9/2002 | Yang et al. | |
| 2002/0133133 | A1 | 9/2002 | Agyapong et al. | |
| 2002/0156442 | A1 | 10/2002 | Jackson et al. | |
| 2003/0028123 | A1 * | 2/2003 | Pevoto | 600/562 |
| 2003/0097108 | A1 * | 5/2003 | Hasse et al. | 604/379 |
| 2003/0167048 | A1 * | 9/2003 | Policappelli | 604/385.17 |
| 2003/0176845 | A1 * | 9/2003 | Kollwitz et al. | 604/385.17 |
| 2003/0211799 | A1 * | 11/2003 | Yao et al. | 442/361 |
| 2004/0049167 | A1 * | 3/2004 | Hasse et al. | 604/385.17 |
| 2004/0193131 | A1 * | 9/2004 | Wada | 604/385.18 |
| 2005/0096620 | A1 * | 5/2005 | Awolin et al. | 604/385.18 |
| 2005/0256484 | A1 * | 11/2005 | Chase et al. | 604/385.18 |
| 2005/0256485 | A1 * | 11/2005 | Carasso et al. | 604/385.18 |
| 2005/0256486 | A1 | 11/2005 | Carasso et al. | |
| 2005/0256511 | A1 | 11/2005 | Chase et al. | |
| 2005/0269220 | A1 * | 12/2005 | Focke et al. | 206/271 |
| 2005/0277904 | A1 * | 12/2005 | Chase et al. | 604/385.18 |
| 2005/0283128 | A1 * | 12/2005 | Chase et al. | 604/378 |
| 2006/0217677 | A1 | 9/2006 | Chase et al. | |
| 2006/0247592 | A1 * | 11/2006 | Schmidt-Forst et al. | 604/385.18 |
| 2007/0010388 | A1 | 1/2007 | Binner | |
| 2007/0049893 | A1 | 3/2007 | Binner et al. | |
| 2007/0282289 | A1 | 12/2007 | Carasso et al. | |
| 2008/0255495 | A1 | 10/2008 | Chase et al. | |
| 2009/0001713 | A1 | 1/2009 | Barker | |
| 2009/0177173 | A1 | 7/2009 | Chase et al. | |

\* cited by examiner

INTRAVAGINAL DEVICE WITH CONTROLLED EXPANSION

This application claims priority to provisional application U.S. Ser. No. 60/584,772, filed Jun. 30, 2004.

CROSS-REFERENCE TO RELATED APPLICATIONS

This invention is related to the following copending applications filed on even date herewith: "Intravaginal Device with Fluid Acquisition Plates" (U.S. Ser. No. 60/572,054), "Intravaginal Device with Fluid Acquisition Plates" (U.S. Ser. No. 10/847,952), "Fluid Management Device with Fluid Transport Element for use within a Body" (U.S. Ser. No. 10/847,951), "Method of Using Intravaginal Device with Fluid Transport Plates" (U.S. Ser. No. 10/848,208), "Tampon with Flexible Panels" (U.S. Ser. No. 10/848,257), and "Method of Using an Intravaginal Device with Fluid Transport Plates" (U.S. Ser. No. 10/848,347), the content of each of which is incorporated herein.

FIELD OF THE INVENTION

The present invention relates to devices for capturing and storing body fluid intravaginally. More particularly, the present invention relates to intravaginal devices that capture body fluid intravaginally by controlling the expansion of the intravaginal device. More particularly, the present invention relates to a tampon having certain predetermined portions capable of expanding during use while other portions remain unexpanded; the expanded portions have less dense regions than the unexpanded portions.

BACKGROUND OF THE INVENTION

Devices for capturing and storing bodily fluid intravaginally are commercially available and known in the literature. Tampons are the most common example of such intravaginal devices.

The tampon is inserted into the human vagina and retained there for a time for the purpose of capturing and storing intravaginal bodily fluids, most commonly menstrual fluid. As intravaginal bodily fluid contacts the tampon, it should be absorbed and retained by the absorbent material of the tampon. After a time, the tampon and its retained fluid is removed and disposed, and if necessary, another tampon is inserted.

Commercially available tampons are generally compressed cylindrical masses of absorbent fibers that may be over-wrapped with an absorbent or nonabsorbent cover layer.

Friese et al., U.S. Pat. No. 4,816,100, discloses a fibrous tampon substantially surrounded by a nonwoven cover material. This tampon expands substantially uniformly over its total length when engaged by fluid. If the fluid is not uniformly or only partially applied to the tampon, increased fluid concentrations are developed in certain regions of the tampon which expand more quickly at these regions in comparison to other regions of the tampon. This leads to a substantially uncontrolled expansion of the tampon, depending only on the fluid concentration on and the fluid distribution to the tampon.

A drawback often encountered with commercially available tampons is the tendency toward premature failure, which may be defined as bodily fluid leakage from the vagina while the tampon is in place, and before the tampon is completely saturated with the bodily fluid. The patent art typically describes a problem believed to occur when an unexpanded, compressed tampon is unable to immediately absorb fluid. Therefore, it presumes that premature leakage may occur when bodily fluid contacts a portion of the compressed tampon, and the fluid is not readily absorbed. The bodily fluid may bypass the tampon.

To overcome this problem of premature leakage, extra elements have been incorporated into a basic tampon to try to control the flow of fluid toward the absorbent core and thereby control the expansion of the absorbent material of the tampon. In most instances, these elements are incorporated into or onto the tampon structure prior to or during compression of the absorbent material.

US Pub. No. 2001/0014348 (Schoelling) discloses a tampon including an absorbent body and a variably perforated or apertured cover. The cover includes a fluid-impervious plastic material in the form of a resilient three-dimensional web having a multiplicity of perforations. The perforations may be varied over the length of the tampon so that a differentiated expansion of the tampon while absorbing fluid is achievable. Preferably, the degree and size of perforations of the cover increases towards the withdrawal end of the tampon at least over a portion of its length. In this embodiment, fluid applied to the tampon is led into the direction of the withdrawal end and results in greater expansion towards the withdrawal end. The cover is attached to the absorbent material during formation and compression of the tampon.

US Pub. No. 2002/0133133 (Agyapong et al.) discloses a tampon having a width, length, and thickness. The tampon is compressed and upon fluid acquisition, provides expansion. The tampons of this publication exhibit an increased width ("X") dimension force with a lower force exhibited in the thickness ("Z") dimension, thereby purporting to provide increased comfort for the wearer. The pledget prior to compression may have shapes such as chevron-like, rectangular, trapezoidal, semi-circular, etc. Preferably, the pledget is shaped such that the middle region is a region having more absorbent material than the top of bottom regions. The pledget undergoes compression primarily focused in the X dimension rather than radially, axially or in multiple dimensions. The pledget material may undergo folding of the absorbent material in the X dimension. Since the human vaginal is typically a flat structure when at rest, the orientation of inserted finished tampon may be important.

Stokes et al. (EP 0 292 831) discloses a spiral wound tampon that is held together by a continuous line of adhesive at what is to be the withdrawal end. This allows for expansion at the insertion end and for removal of the tampon from the body cavity without telescoping. The withdrawal end remains in the original unexpanded state.

Others have included additional or secondary absorbent elements on the withdrawal string or even the finished tampon. See, for example, U.S. Pat. No. 3,101,714 (Penska) and U.S. Pat. No. 6,258,075 (Taylor et al.). Unfortunately, the secondary absorbent element may affect comfort of the wearer as it is close to vaginal opening.

Other may incorporate portions or projections that extend and contact the vaginal walls. See, for example, U.S. Pat. No. 4,212,301 (Johnson); U.S. Pat. No. 6,358,235 (Osborn et al.); U.S. Pat. No. 6,177,608 (Weinstrauch); and U.S. Pat. No. 6,206,867 (Osborn). None of the above mentioned disclosures disclose a predetermined expansion of the absorbent core in order to control the absorption of fluid.

While the prior art is replete with examples of sanitary protection articles is that capture bodily fluids intravaginally, these examples do not overcome the problem of premature failure often identified as by-pass leakage that commonly occurs while using internal sanitary protection devices. Many solutions to this problem have involved adding elements before the tampon pledget is compressed and hence the expansion of the tampon when body fluid contacts it is not controlled. The present invention details a way to control expansion such that only certain portions of the tampon expand when exposed to body fluid.

SUMMARY OF THE INVENTION

We have found a novel way to address the problem of premature failure by controlling the expansion of the intravaginal device. By selectively attaching either a primary or secondary cover to the primary absorbent device having a fluid storage element, we can determine that certain portions of the tampon will expand while other portions will be restricted to substantially the compressed structure. The primary cover can be attached to the primary absorbent device either before or after the absorbent device is compressed into final tampon form. The compression may be in the axial or radial direction or a combination of both directions. The secondary cover, if used, can be attached after the tampon pledget has been compressed into the final tampon form.

In one embodiment, an intravaginal device has a fluid storage element including a compressed absorbent web and a primary cover. The primary cover is attached to the compressed fluid storage element to restrict substantial expansion of at least one portion of the fluid storage element when exposed to bodily fluid.

In another embodiment, an intravaginal device has a compressed fluid storage element including an absorbent web and a primary cover attached to the fluid storage element. The primary cover includes one or more shrinkable materials and/or binding agents that restrict substantial expansion of at least one portion of the fluid storage element when exposed to bodily fluid.

In yet another embodiment, an intravaginal device has a compressed absorbent element with a fluid storage element and a primary cover and a secondary cover. The secondary cover is attached to the absorbent device to restrict substantial expansion of at least one portion of the fluid storage element when exposed to bodily fluid.

DETAILED DESCRIPTION OF THE PREFERRED EMBODIMENTS

Figure 1:
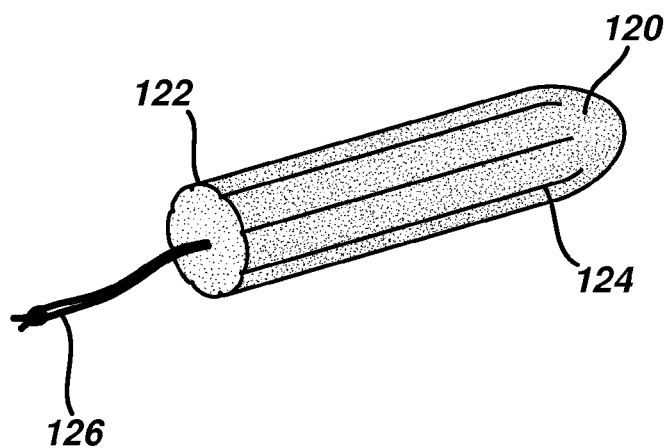
FIG. 1 shows a perspective view of a compressed tampon having a cover substantially encasing a fluid storage element.

As used herein in the Specification and the Claims, the term "bodily fluid" and variants thereof mean bodily exudates, especially liquids that are produced by, secreted by, emanate from, and/or discharged from a human body.

As used herein in the Specification and the Claims, the term "fluids" and variants thereof relate to liquids, and especially bodily fluids.

As used herein in the Specification and the Claims, the term "in fluid communication" and variants thereof relate to elements that are arranged and configured to allow fluid to move therebetween. The fluid movement may be by interfiber capillary movement, intrafiber capillary movement, osmotic pressure, interplate capillary action, mechanical channeling, and the like.

As used herein, the term fluid storage element relates to any absorbent medium that forms the absorbent portion of the intravaginal device. In a tampon, the fluid storage element could also be known as the absorbent core. The fluid storage element may have a single density or may have portions that have different densities. For example, the fluid storage element may have a central portion having a high density and an outer layer that is less dense.

This invention relates to devices 10 (e.g., intravaginal tampons) for capturing and storing bodily fluid. More particularly, the invention relates to an improved intravaginal device 10 that has a compressed core portion that expands when fluid contacts the core material. The core material may primarily contain absorbent material. The cover 14, including a primary and/or a secondary cover 16 and 18, respectively, is attached to the core such that the core can only expand as much as the cover material can stretch. Thus the cover 14 can impede or control expansion.

The cover 14, including the primary and/or secondary cover 16 and 18, respectively, may be attached to the fluid storage element 12 in different ways or may impact the fluid storage element 12 in different ways. For example, the cover 14 may be attached after the fluid storage element 12 has been compressed and formed into a form that may be inserted into the body. In another embodiment, the cover 14 is attached prior to compression but the cover 14 is made from material that for example, forms a rigid outer shell that does not expand or stretch to allow the absorbent material encased to expand to a lower density. In still another embodiment, the cover 14 may contain a binding material such that the cover 14 is bond to the absorbent material, forming a "set" attachment, which does allow for expansion or stretching of the cover material.

In this invention, different degrees of expansion are obtainable by the degree in which the primary cover 16 is attached to the fluid storage element 12. If the primary cover 16 is attached such that the absorbent material is tightly held to its original compressed structure, the density of the fluid storage element 12 substantially remains the same during and after exposure to bodily fluids. The amount of fluid absorbed and contained by the fluid storage element 12 can be greatly restricted if the density of the material is not allowed to change. In another embodiment, the density of the fluid storage element 12 may vary throughout the structure. For example, in one portion of the fluid storage element 12 the density may remain closer to the original pre-insertion state but in another, expanded portion, the fluid storage element 12 density would decrease as the volume increases. For example, the density of the first portion may remain close to 0.4 g/cc, while the density of the expanded, second portion may decrease, e.g., below 0.3 g/cc.

If it is desired that the fluid storage element 12 be capable of absorbing fluid, then it may be desirable for the fluid storage element 12 to expand and go from a high density to a lower density, thereby forming spaces and voids in which the fluid may be contained within and by the absorbent material.

Referring to FIG. 1, a tampon of the prior art is shown. In this example, intravaginal device 120 has fluid storage element 122, cover 124, and withdrawal mechanism 126. In this tampon, cover 124 substantially encases the fluid storage element 122. Typically, the fluid storage element 122 or absorbent core is made from a calendared nonwoven ribbon of absorbent material that has a liquid-permeable, thermoplastic strip section attached to it along parallel bonds extending obliquely relative to the longitudinal direction of the nonwoven ribbon. The combined nonwoven ribbon section with attached thermoplastic strip is essentially rolled up on itself, forming a tampon blank or pledget. The tampon blank is subsequently compressed in a tampon press into final form as shown in FIG. 1.

FIGS. 2-6 illustrate examples of the present invention. These figures show an intravaginal device after controlled expansion. For example, a dry, unexpanded intravaginal device useful in this invention may have the general appearance, shape, and configuration of the tampon of the prior art prior to insertion and as shown in FIG. 1. FIGS. 2-6 illustrate possible embodiments of the invention after controlled expansion, i.e., certain portions of the fluid storage device remain compressed while selected portions expand after exposure to bodily fluid.

Turning to FIGS. 2-6, an intravaginal device 10 is provided having at least a primary cover 16 in fluid communication with a fluid storage element 12. The device may also include an insertion portion 22, a central portion 24, withdrawal portion 26, and a withdrawal mechanism 20, such as a string.

Figure 2:
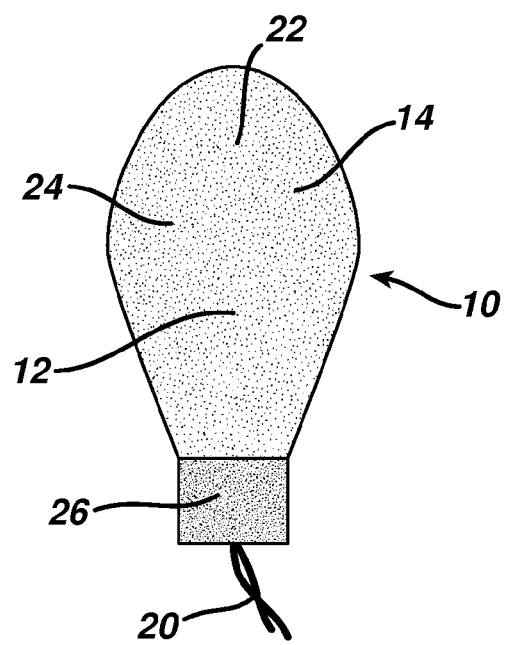
FIG. 2 shows a side elevation of one embodiment of the present invention where the expanded tampon has a cover restricting expansion at the withdrawal portion of the tampon.

FIG. 2 illustrates an example of a tampon in which the primary cover 16 has been attached such that upon absorption of fluid, insertion portion 22 and central portion 24 of the intravaginal device 10 are able to expand while the withdrawal portion 26 remains unexpanded. It is assumed that the density of the withdrawal portion 26 is higher than the insertion portion 22 and central portion 24 after fluid absorption.

Figure 3:
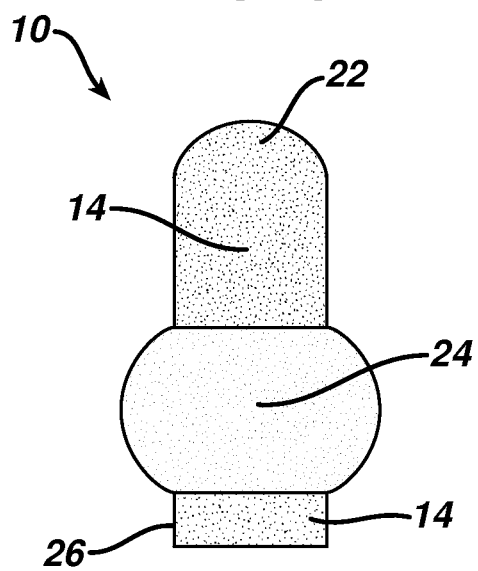
FIG. 3 shows a side elevation of an alternate embodiment of the present invention where the expanded tampon has a cover restricting expansion at the insertion and withdrawal portion of the tampon.

FIG. 3 shows an example of a tampon in which the cover 14 has been attached such that expansion is limited at a longitudinally extending, generally cylindrical, insertion portion 22 and at a longitudinally extending, generally cylindrical, withdrawal portion 26, leaving a longitudinally extending, generally cylindrical, central portion 24 capable of expanding upon exposure of fluid.

Figure 4:
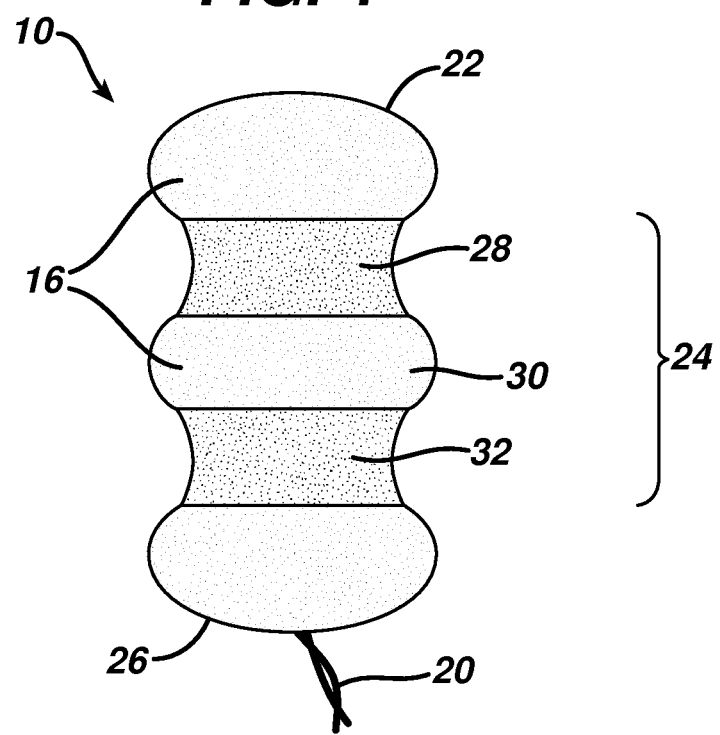
FIG. 4 shows a side elevation of still another embodiment of the present invention where the expanded tampon has a cover restricting expansion at the multiple portions of the tampon.

FIG. 4 shows another example of selective expansion. In this embodiment, cover restricts expansion in at least two longitudinally extending, generally cylindrical, portions of the fluid storage element 12. Central portion 24 has three longitudinally extending, generally cylindrical, portions: upper zone 28, mid zone 30 and lower zone 32. Cover has been attached such that upper zone 28 and lower zone 32 remain unexpanded while mid zone 30 is allowed to expand upon exposure to fluid.

Figure 5:
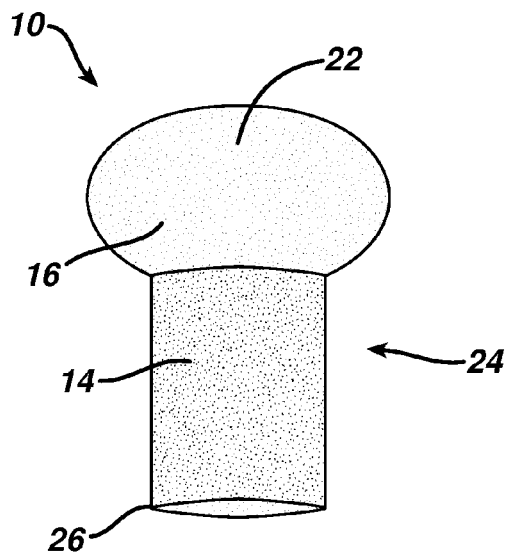
FIG. 5 shows a side elevation of still another embodiment of the present invention where the expanded tampon has a cover restricting expansion at the withdrawal portion of the tampon.

FIG. 5 shows still another example of selective expansion. In this embodiment, cover 14 restricts expansion of longitudinally extending, generally cylindrical, central portion 24 and longitudinally extending, generally cylindrical, withdrawal portion 26 remain unexpanded while longitudinally extending insertion portion 22 is allowed to expand.

Figure 6:
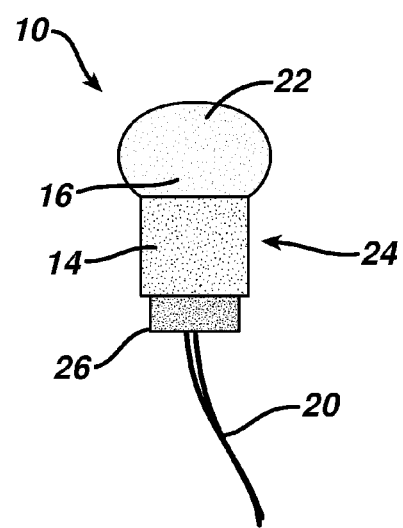
FIG. 6 shows a side elevation of still another embodiment of the present invention where the expanded tampon has a cover restricting expansion at the multiple portions of the tampon including the withdrawal portion and the central portion.

FIG. 6 shows yet another embodiment of selective expansion. In this embodiment, cover 14 restricts expansion of longitudinally extending, generally cylindrical, withdrawal portion 26 remains while longitudinally extending, generally cylindrical, central portion 24 has been allowed to partially expand.

Longitudinally extending insertion portion 22 has expanded to a greater degree than central portion 24.

The figures show examples of embodiments in which the primary cover 16 is used to control expansion. Alternately, a secondary cover 18 may be used.

If the fluid storage element 12 is a compressed tampon having embossed grooves 36 such as those disclosed in U.S. Pat. No. 5,165,152 the disclosure of which is hereby incorporated by reference, the attachment of the secondary cover 18 may be on the outer most surface (non-embossed) or in the grooves 36. Attachment may take place during pre or post compression/embossment of the tampon.

Alternative manufacturing processes are disclosed in U.S. Pat. No. 4,816,100 and U.S. Pat. No. 6,310,269, the disclosures of which are hereby incorporated by reference.

Figure 7:
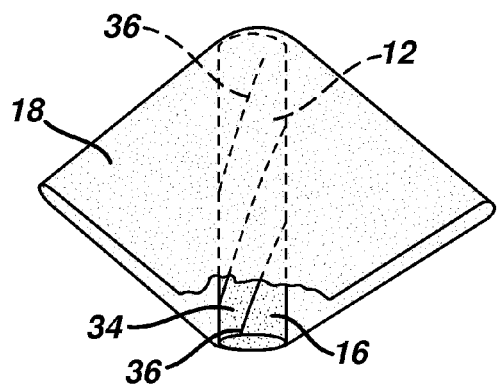
FIG. 7 shows a side elevation of another embodiment of the present invention wherein the intravaginal device includes a secondary cover.

As disclosed in co-pending application PPC-5072 filed May 14, 2004, a secondary cover 18 may be attached to a finished tampon. The secondary cover 18 may be attached to the insertion portion, withdrawal portion or along the longitudinal sides of the tampon. In the prior application, the attachment was such that the expansion of the absorbent material was not affected, that is, the tampon was not limited by the attachment or actual binding of the secondary cover 18 to the primary cover 16 or absorbent material of the tampon. As seen in FIG. 7, the intravaginal device 10 is a compressed tampon having an outward surface 34 and grooves 36. Grooves 36 have inward surface. Intravaginal device 10 has a primary cover 16 that is attached to fluid storage element 12. The secondary cover 18 envelopes the insertion end of the compressed tampon. The attachment of the secondary cover 18 to primary cover 16 is such that the attachment to outward surface 34 crosses over at least one of the grooves 36 and thereby restricts the expansion of the overall intravaginal device 10. The attachment may also extend into the groove(s) 36 to the inward surface.

In another embodiment (not shown), the primary cover is similarly attached as the secondary cover 18 is to the fluid storage element 12 as in FIG. 7. That is, the fluid storage element 12 is compressed without a cover. The cover 14 including primary cover 16 is then attached to the fluid storage element 12 in specific spots that inhibit expansion.

When a compressed tampon having grooves 36 is used as the fluid storage element 12, it may be possible to inhibit expansion. While some compressed tampons expand due to dry expansion, others expand when exposed to fluid. One example of such a compressed tampon having grooves 36 is a commercially available O.b.® tampon. When the cover 14 is attached to a compressed tampon having grooves 36, the attachment may constrict the material in the grooves 36 from expanding.

As previously described, materials such as apertured films have a certain amount of elasticity and may or may not constrict the expansion of the tampon, especially the material located within the groove. The material used to form the cover 14 must be chosen with care depending on the desired expansion of the fluid storage element 12.

In particular, materials useful for forming the primary and secondary covers need to have qualities such as thermobondability so that it may become part of the intravaginal device.

A representative non-limiting list of useful materials includes polyolefins, such as polypropylene and polyethylene; polyolefin copolymers, such as ethylenevinyl acetate ("EVA"), ethylene-propylene, ethyleneacrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. The cover 14 may also be micro-embossed or apertured. Examples of films having apertures include for example, three-dimensional apertured films, as disclosed in Turi et al, U.S. Pat. No. 5,567, 376, and two-dimensional reticulated film, such as that described in Kelly, U.S. Pat. No. 4,381,326.

It may be helpful to keep the exposed outer surface of the cover 14 as smooth as possible. It may also be helpful to provide it with a low a coefficient of friction. These characteristics provide at least two benefits: (1) the force required to insert the intravaginal device is reduced, and (2) it reduces the damage otherwise caused by scraping of soft, tender vaginal tissue during insertion, wearing and removal.

The primary and/or secondary cover 16 and 18, respectively, should be strong enough to prevent rupturing during handling, insertion, and removal and from vaginal pressures during use. If a secondary cover 18 is used, it need not be the same material as the primary cover material.

Materials known in the art to have low energy surfaces may be used. It is also possible and useful to coat materials with high-energy surfaces with a surface additive, such as a non-ionic surfactant (e.g., ethoxylates), a diol, or mixtures thereof, in order to increase their wettability by bodily fluids. Such additives are well known in the art, and examples include those described in Yang et al., US App. No. 2002-0123731-A1, and U.S. Pat. No. 6,570,055. Other means of increasing wettability can also be used, such as by corona discharge treatment of, for example, polyethylene or polypropylene, or by caustic etching of, for example, polyester.

It is preferred that the apertures are large enough to let viscous fluid pass through but not too large to create too rough of a surface as to compromise the wearer's comfort.

Open area may be determined by using image analysis to measure the relative percentages of apertured and unapertured, or land, areas. Essentially image analysis converts an optical image from a light microscope into an electronic signal suitable for processing. An electronic beam scans the image, line-by-line. As each line is scanned, an output signal changes according to illumination. White areas produce a relatively high voltage and black areas a relatively low voltage. An image of the apertured formed film is produced and, in that image, the holes are white, while the solid areas of thermoplastic material are at various levels of gray. The more dense the solid area, the darker the gray area produced. Each line of the image that is measured is divided into sampling points or pixels. The following equipment can be used to carry out the analysis described above: a Quantimet Q520 Image Analyzer (with v. 5.02B software and Grey Store Option), sold by LEICA/Cambridge Instruments Ltd., in conjunction with an Olympus SZH Microscope with a transmitted light base, a plan 1.0× objective, and a 2.50× eyepiece. The image can be produced with a DAGE MTI CCD72 video camera.

A representative piece of each material to be analyzed is placed on the microscope stage and sharply imaged on the video screen at a microscope zoom setting of 10×. The open area is determined from field measurements of representative areas. The Quantimet program output reports mean value and standard deviation for each sample.

The primary cover 16 is in fluid communication with the fluid storage element 12 and directs fluid from the vagina to the fluid storage element 12. Generally, fluid will be directed from the cover 14 to the fluid storage element 12. The secondary cover 18, if used, is also in fluid communication with the primary cover 16 or with the fluid storage element 12 if the primary cover 16 does not completely cover the fluid storage element 12. For example, primary cover 16 may wrap around the sides of the fluid storage element 12 and not encase insertion portion 22 while secondary cover 18 may drape over fluid storage element 12, including the insertion portion, and be attached along the longitudinal sides or withdrawal portion 26.

The ability of the cover 14 to direct fluid to additional or less dense locations of the fluid storage elements 12 will improve the efficient usage of the fluid storage element 12.

For example, the fluid storage element 12 may have a withdrawal portion that the cover 14 has been completely attached around such that the fluid storage element 12 is restricted in expansion at this portion. The cover 14 may not be bonded to the insertion or central portion of the fluid storage element 12 and hence the insertion and central portion may have the ability to expand upon exposure to fluid. An example of this embodiment may be seen in FIG. 2. Turning to the figure, it can be seen that the central portion 24 and insertion portion 22 are expanded such that the withdrawal end 26 appears to be narrow and much more restricted.

The density of the insertion portion 22 and central portion 24 is less than the density of the withdrawal portion 26.

While the above description provides for direct fluid communication between the fluid storage element 12 and the primary and/or secondary covers 16 and 18, respectively, direct fluid contact is not necessary. There can be fluid communication through an intermediate element, such as a foam or fibrous structure.

The primary or secondary covers 16 and 18, respectively, may be attached directly to the fluid storage element 12 or may be attached to itself in one or more locations as long as the attachment is capable of restricting expansion of the fluid storage element 12. Such attachment or adherence to itself or to the fluid storage element 12 may be by any known means, including, for example, adhesive, ultrasonics, co-embossing, thermobonding, mechanical bonding, and the like. In one embodiment, the fluid transport element is formed of a material that is capable of being thermobonded together. Alternately, the material may formed of two different materials having different melting points, which would also be capable of thermobonding.

It is not necessary for the fluid storage element 12 to be a unitary element. For example, the fluid storage element 12 may have multiple distinct portions or segments. The segments may be attached together or may be discrete. Examples of discrete segments may be relatively loose absorbent material, a series of compressed segments or compressed cellulosic pellets.

The material used to form the primary or secondary covers 16 and 18, respectively, may initially be in a shape such that the sheet has at least one corner. The cover material may be placed over the fluid storage element 12 such that a corner may be formed.

Attachment of the primary or secondary cover 16 and 18, respectively, may be in any direction relative to the fluid storage element 12. For example, the cover including the primary cover 16 or secondary cover 18 may be attached by a series of heat embossments that form a single line pattern from the insertion portion to the withdrawal portion. In another embodiment, the attachment is by means of a series of dots.

In one instance the tampon blank does not have a primary cover; in another embodiment, the tampon blank has a primary nonwoven cover 16. In still another embodiment, the tampon has an apertured film cover as described in co-pending, commonly assigned U.S. Ser. No. 09/345,090, filed Jun. 30, 1999, the disclosure of which is hereby incorporated by reference.

The fluid storage element 12 may take any form such as, for example commercially available absorbent tampons made by McNeil PPC, Inc., Playtex, Kimberley-Clark, Tambrands, and Procter & Gamble. In particular, when the cover encases the fluid storage element 12 and is sealed to itself, the fluid storage element 12 may be either compressed, non-compressed, unitary, or segmented as previously discussed. For the fluid storage element 12 to be effective, it may be critical that the expansion of the fluid storage element 12 (tampon) not be affected by the attachment of the fluid transport element.

The fluid storage element 12 can be any convenient shape including cylindrical, cup like, hourglass, spherical, etc. It can be an absorbent or a fluid collection device. It can be made of any composition known in the art, such as compressed fibrous webs, rolled goods, foam etc. The storage element can be made of any material known in the art such as cotton, rayon, polyester, SAP etc.

The fluid storage element 12 can be in separate sections with the parallel plates bridging or connecting the sections.

In one preferred embodiment, the fluid storage element 12 is an absorbent tampon. Absorbent tampons are usually substantially cylindrical masses of compressed absorbent material having a central axis and a radius that defines the outer circumferential surface of the tampon. Such tampons are disclosed in e.g., Haas, U.S. Pat. No. 1,926,900; Dostal, U.S. Pat. No. 3,811,445; Wolff, U.S. Pat. No. 3,422,496; Friese et al., U.S. Pat. No. 6,310,296; Leutwyler et al., U.S. Pat. No. 5,911,712, Truman, U.S. Pat. No. 3,983,875; and Agyapong et al., U.S. Pat. No. 6,554,814 (the disclosures of which are herein incorporated by reference). Tampons also usually include a cover 14 or some other surface treatment and a withdrawal string or other mechanism 20.

Absorbent materials useful in the formation of the absorbent body include fiber, foam, superabsorbent, hydrogels, and the like. Preferred absorbent material for the present invention includes foam and fiber. Absorbent foams may include hydrophilic foams, foams that are readily wetted by aqueous fluids as well as foams in which the cell walls that form the foam themselves absorb fluid.

Preferably, the fibers employed in the formation of the absorbent body include regenerated cellulosic fiber, natural fibers, and synthetic fibers. Preferably, the materials employed in the formation of a tampon according to the present invention include fiber, foam, hydrogels, wood pulp, superabsorbents, and the like. A useful, non-limiting list of useful absorbent body fibers includes natural fibers such as cotton, wood pulp, jute, and the like; and processed fibers such as regenerated cellulose, cellulose nitrate, cellulose acetate, rayon, polyester, polyvinyl alcohol, polyolefin, polyamine, polyamide, polyacrylonitrile, and the like. Other fibers in addition to the above fibers may be included to add desirable characteristics to the absorbent body. Preferably, tampon fibers are rayon or cotton, and more preferably, the fibers are rayon. The fibers may have any useful cross-section.

Fibers may be selected from cellulosic fiber, including natural fibers (such as cotton, wood pulp, jute, and the like) and synthetic fibers (such as regenerated cellulose, cellulose nitrate, cellulose acetate, rayon, polyester, polyvinyl alcohol, polyolefin, polyamine, polyamide, polyacrylonitrile, and the like).

Tampons are generally categorized in two classes: applicator tampons and digital tampons, and a certain amount of dimensional stability is useful for each type of tampon. Applicator tampons use a relatively rigid device to contain and protect the tampon prior to use. To insert the tampon into a body cavity, the applicator is partially inserted into the body cavity, and the tampon can be expelled therefrom. In contrast, digital tampons do not have an applicator to help guide them into the body cavity and require sufficient column strength to allow insertion without using an applicator.

While the applicator tampon is protected by the rigid applicator device and the applicator tampon need not as have high a degree of column strength as a digital tampon, applicator tampons do require dimensional stability (especially radial) to be acceptable for use. This dimensional stability provides assurance, for example, that the tampon will not prematurely grow and split its packaging material or become wedged in a tampon applicator.

A withdrawal mechanism 20, such as a string, is preferably joined to the intravaginal device 10 for removal after use. The withdrawal mechanism 20 is preferably joined to at least the fluid storage element 12 and extends beyond at least its withdrawal portion 26. Any of the withdrawal strings 20 currently known in the art may be used as a suitable withdrawal mechanism, including without limitation, braided (or twisted) cord, yarn, etc. In addition, the withdrawal mechanism 20 can take on other forms such as a ribbon, loop, tab, or the like (including combinations of currently used mechanisms and these other forms). For example, several ribbons may be twisted or braided to provide parallel plates structures.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. An intravaginal device having controlled expansion comprising a fluid storage element having an insertion end, an opposite withdrawal end, and a central portion therebetween comprising:
   a. a compressed absorbent element having a first density;
   b. a primary cover attached to an outer cylindrical surface of the fluid storage element; and
   c. a secondary cover disposed over at least the insertion end of the fluid storage element
   wherein the secondary cover comprises a sheet of thermobondable apertured film material, completely envelopes the insertion end, and is attached to the absorbent element to restrict at least one portion of the fluid storage element when exposed to bodily fluids,
   wherein the at least one portion is disposed in at least one of the central portion, the insertion end, and the withdrawal end of the fluid storage element, and wherein the at least one portion is a longitudinally extending, generally cylindrical portion enveloped by substantially non-expandable portion of the thermobondable apertured film material that has a volume that remains substantially constant after exposure to bodily fluids and wherein a second portion of the fluid storage element has a volume that increases upon exposure to bodily fluids.

2. The intravaginal device of claim 1, wherein at least one of the primary cover and secondary cover has a plurality of regions comprising at least a first region and a second region, wherein said first region has at least one physical characteristic that differs from the same at least one physical characteristic of said second region.

3. The intravaginal device of claim 2, wherein the secondary cover has a plurality of regions comprising at least a first region and a second region, wherein said first region has an elongation characteristic that differs from an elongation characteristic of said second region.

4. The intravaginal device of claim 2, wherein the secondary cover has a plurality of regions comprising at least a first region and a second region, wherein said first region has a machine direction elongation characteristic that differs from a machine direction elongation characteristic of said second region.

5. The intravaginal device of claim 2, wherein the secondary cover has a plurality of regions comprising at least a first region and a second region, wherein said first region has an elongation aligned perpendicular to a machine direction characteristic of the primary cover material that differs from an elongation aligned perpendicular to a machine direction characteristic of the primary cover material of said second region.

6. The intravaginal device of claim 1, wherein the secondary cover comprises a binder material.

7. The intravaginal device of claim 1, wherein the secondary cover is arranged and configured to restrict expansion of at least the insertion end.

8. The intravaginal device of claim 1, wherein the device has an insertion end, an opposite withdrawal end, and a central portion therebetween, and the secondary cover is arranged and configured to restrict expansion of at least the central portion.

9. The intravaginal device of claim 1, wherein the device has an insertion end, an opposite withdrawal end, and a central portion therebetween, and the secondary cover is arranged and configured to restrict a plurality of regions in the central portion.

10. The intravaginal device of claim 1, wherein the second portion of the fluid storage element that has a volume that increases upon exposure to bodily fluids is a longitudinally extending portion.

* * * * *